United States Patent [19]

Pan et al.

[11] Patent Number: 5,846,975

[45] Date of Patent: Dec. 8, 1998

[54] USE OF AMINO HYDROGENATED QUINAZOLINE COMPOUNDS AND DERIVATIVES THEREOF FOR ABSTAINING FROM DRUG DEPENDENCE

[75] Inventors: Xinfu Pan, Beijing; Fanglong Qiu, Hunan, both of China

[73] Assignee: Nanning Maple Leaf Pharmaceutical Co., Ltd., Guangxi Province, China

[21] Appl. No.: 640,781

[22] PCT Filed: Mar. 11, 1995

[86] PCT No.: PCT/CN95/00016

§ 371 Date: May 21, 1996

§ 102(e) Date: May 21, 1996

[87] PCT Pub. No.: WO95/24903

PCT Pub. Date: Sep. 21, 1995

[30] Foreign Application Priority Data

Mar. 17, 1994 [CN] China ............................. 94 1 10873.2

[51] Int. Cl.⁶ ................................................. A61K 31/505
[52] U.S. Cl. ............................................................ 514/282
[58] Field of Search ..................................... 514/260, 282

[56] References Cited

U.S. PATENT DOCUMENTS 3,898,339  8/1975  Adams et al. ........................... 424/251
5,474,547  12/1995  Aebisher et al. ....................... 604/891

FOREIGN PATENT DOCUMENTS

B41-010330  6/1966  Japan .
B44-010903  6/1966  Japan .
B44-010904  6/1966  Japan .
B44-010906  6/1966  Japan .
B42-009355  5/1967  Japan .
B42-009356  5/1967  Japan .
1370905  10/1974  United Kingdom .

OTHER PUBLICATIONS

Y. Kishi et al., *J. Am. Chem. Soc.*, 94:26, pp. 9217–9221 (Dec. 27, 1972).
T. Goto et al., *Tetrahedron*, vol. 21, pp. 2059–2088 (1965).
E. Murtha et al., *Journal of Pharmacology and Experimental Therapeutics.*, vol. 122, pp. 247–254 (1958).
Chemical Abstracts AN 1977: 268, Fredrikson et al, 1976.

*Primary Examiner*—Keith D. MacMillan
*Attorney, Agent, or Firm*—Birch, Stewart, Kolasch & Birch, LLP

[57] ABSTRACT

This invention relates to the use of amino hydrogenated quinazoline compounds and derivatives thereof, such as tetrodotoxin, for abstaining from drug dependence in human. Such compounds are administered by subcutaneous, intramuscular or intravenous injection for abstaining from drug dependence, the said drug is alkaloids and nitrogen-containing non-amino acid compound, for example opium, morphine, heroin and the like. Such compounds without drug dependence and low toxicity and side effect can abstain rapidly from drug dependence.

22 Claims, No Drawings

5,846,975

USE OF AMINO HYDROGENATED QUINAZOLINE COMPOUNDS AND DERIVATIVES THEREOF FOR ABSTAINING FROM DRUG DEPENDENCE

TECHNICAL FIELD

This invention is concerned with amino hydrogenated quinazoline compounds and derivatives thereof, particularly their new application for causing humans to abstain from drug dependence on alkaloids and synthetic non-amino acid nitrogen.

BACKGROUND OF THE INVENTION

The research of amino-hydro quinazoline and its derivatives originated from the knowledge for crystal tetrodotoxin (TTX).

TTX is a well-known amino-perhydro quinazoline with its molecular formula as $C_{11}H_{17}N_3O_8$ and its molecular weight 319.27. The chemical structure for TTX is shown as following:

TTX has been found in many puffers up to one hundred, such as tetrodontidae, diodontidae, molidae, triodontidae and other families of puffer. These puffers are classified as hard-fish sub-class, fish class. Tissues of these puffers rich in TTX include ovary, liver, skin, and gastrointestinal. Methods of TTX extracting from these tissues have been reported by T. Goto et al. (Tetrohedron, 21, 2059. 1965) and E. F. Murtha (Expte. Therap., 122, 246. 1958). For TTX synthesis method, see Y. Kishi, et al., J. Am. Chem. Soc., 94(26), 9217, 9219. 1972. Later studies revealed that TTX and its derivatives could be detected in amphibians like salamanders, in mollusks like octopus, shellfish, and snails, in arthropods like crabs, limulus, starfish and in plants like red algae. Very recently, it was found that TTX was also produced by some geneses bacteria such as vibros, pseusdomona, streptomyces josamycetinus and etc. TTX is an extreme poison whose toxicity is 1,250 times more than that of sodium cyanide. It was estimated that dosage of TTX as little as 0.5 mg could bring death of a person with 70 kg body weight. In another report, subcutaneous injection of 300 μg TTX was enough to put death of a man with 50 kg body weight.

Although TTX has been long recognized, its clinical indications limit in following aspects:
1. Analgesia (1). TTX produces pronounced analgesic effect on various pains caused by burning, trauma, injuries from falls, fractures, contusions and strains, especially for neuragia, myalgia and arthralgia. Unless the diseases are inveterate, TTX is a powerful analgesic.

(2). Local anesthesia

TTX can be used as local anesthetic and is ten thousandfold more powerful than those commonly used local narcotics (Kao CY and Fulman FA, J. Pharmacol., 140, 31–40, 1965). The combined preparations of TTX with widely-used local anesthetics have been published in U.S. Pat. No. 4,022,899 and U.S. Pat. No. 4,029,793.

(3). As a potent analgesic for late cancer patients. TTX exerted satisfactory effect of pain relieving on cancer pain, and no drug addiction cases were reported [Kao C Y, Pharm. Rev. 18(2):997, 1966]

2. Sedation (1) As antipruritic for winter skin itch, prurigo, thylacitis, itch mite and sarcoptic mite. It also facilitated recovery from these dermatosises.

(2) As asthma and pertusis abirritant.

(3) As enuresis inhabitant.

3. Antispasmodic

TTX is an effective antispasmodic for myospasm, gastrospasm and other kinds of spasms, particularly for tetanospasm.

4. Blood pressure depressor

TTX produced strong depressing effect on blood pressure, for example, administration of 2–3 μg/kg TTX to the cat (i.v.) could abruptly lower its arterial pressure as much as two thirds of the normal value, and the duration of it action is fairly short, these characteristics possibly make it useful in first aid of hypertension crisis in the clinic.

5. Others (1) TTX was reportedly effective on pain relieving for lepers (Nomiyama S: Fed. Proc.31:1 117,1972)

(2) Due to its function of congestion, TTX can elicit therapeutic effect on man's impotence and woman's asexuality.

Up to now, no applications of TTX, amino hydrogenated quinazoline compounds and derivatives thereof in abstaining from drug dependence have been reported in prior art. Here, the conception of drug dependence refers to such a physical (or physiological) state of subjects as we call it, withdrawal syndrome, which is produced by everlasting interaction between the body and drug, the symptoms include perspiration, lacrimation, yawn, rigor, goose flesh, mydriasis, vomiting, diarrhea, achycadia, hypertension, insomnia, mania, remor and etc. Subjects are obliged to use drugs continuously not for therapeutic aim but for abuse which occurs once drugtaking is stopped. Drugs here mentioned refer to alkaloids part of drugs, such as opium, morphine, cocaine, amphetamine, and other synthetic non-amino acid nitrocompounds, such as heroin, dolantin, dihydroetorphine, methadone, and etc.

The frightening consequences of drug abuse make it desperately needed for the society to develop new de-addiction drugs which are highly effective, short of severe side reactions.

So far, the methods for addiction therapy in the world mainly rely on substitutive drugs. Briefly, they can be summarized as follows:

1. Taking small dose of opium-containing drugs. During the therapy period, opium may be gradually reduced till no opium is used in the end. This regimen lasts quite long (16 days), and its curative effect is just so-so.

2. Taking methadone orally. Methadone is used as a substitution for abused drugs like opiums. This therapy is currently applied as a standard treatment for drug abuse, most patients can free themselves from drug dependence within 10 days.

3. Using dehydroetorphine(DHE). According to clinical trials, dose-reducing therapy of DHE could alleviate abstinence symptoms within 7 to 10 days, however, during the therapy period, DHE dependence usually occurred.

4. Administration of buprenorphine.
5. Other drugs, like clinidine.

Recently, the combination of drugs above mentioned has been coming into use, for example, DHE combined with methadone was used for heroin addiction [Sha Lijun et al. Xinyao he Linchuang (New Drugs and Clinical Remedies) 13(6), 337–339, 1994], and also small dose of DHE combined with anisodaminum possessed the same therapeutic effect for heroin dependence [Su Mujing et al.Chinese Drug Dependence Bulletin, 2(1): 48–51, 1992]. In addition, anisodaminum alone or plus chlorpromazine were also used for de-addiction therapy.

Among above drugs, methadone, and DHE are themselves addictive medicine if used for a long time. Anisodaminum, though lack of addictive, can produce various side effects, such as blurred vision, airway secreta drying, thirst, enuresis and etc. For these reasons, it is imperative to seek new de-addiction drugs which are highly effective, lack drug dependence and severe side reactions.

The object of the present invention is to provide a novel application of amino hydrogenated quinazoline compounds and derivatives thereof, including TTX, to cause humans to abstain from drug dependence on alkaloids.

The other object of the invention is to provide a pharmaceutical composition containing amino hydrogenated quinazoline compounds and derivatives thereof for the same therapeutic use as above.

The further object of the invention is to provide methods of causing humans to abstain from alkaloids dependence by administering amino hydrogenated quinazoline compounds and derivatives thereof to human patients.

DISCLOSURE OF INVENTION

The present invention relates to a use of amino hydrogenated quinazoline and derivatives thereof are compounds having the general formula I in the preparation of medicament for causing humans to abstain from drug-dependence,

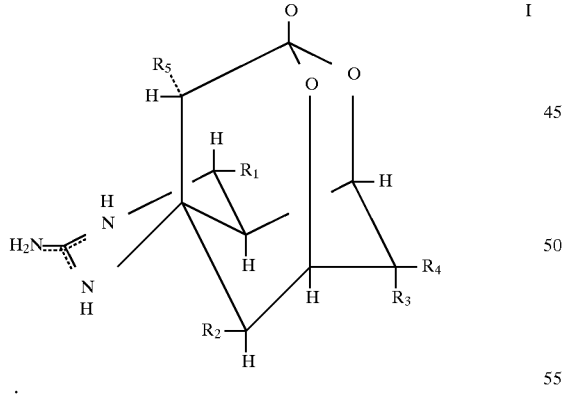

wherein, $R_2$ and $R_5$ can be selected from the group consisting of H, OH, OAC, respectively;

$R_1$ call be H, or an alkyl with $C_1$–$C_4$, OH, OR, OC(O)R', $NH_2$, NHR'', NR''R''', among them R can be an alkyl with $C_1$–$C_6$, R' can be an alkyl with $C_1$–$C_3$, and R'', R''' can be an alkyl with $C_1$–$C_4$, respectively;

$R_3$ and $R_4$ can be =O, or when $R_3$ is H, $R_4$ can be selected from the group consisting of:

—ROH, and R is a branched or straight chain alkyl with $C_1$–$C_7$,

—CH(OH)NHOMe,
—NAP—gly,
—NAP—en,
—$CH_2NH_2$,
$CH_2NHCH_3$,
—AAG,
—NMAG, and
—ANT;

when $R_3$ is OH or OC(O)R and R is an alkyl with $C_1$–$C_3$, $R_4$ can be selected from the group consisting of:

—CHO,
—$CH_2$—gly,
—$CH_2$—β—Ala,
$CH_2$—Lys,
—$CH_2$—en,
—$CH_2$—NAP—Lys,
—$CH_2$—NAP—en,
—CH(OH)CH($NH_2$)COOH; and,
—NH($CH_2$)$_n$COOH,
—NH($CH_2$)$_n$$NH_2$; and
—NH($CH_2$)$_n$CH($NH_2$)COOH, wherein:

n=1–6.

en is ethylene;

NAP is 4-triazo-2-nitrobenzoic amide, indicated as formula (a);

AAG is 2-triazo-O-aminobenzoic amide, indicated as formular (b);

NMAG is O-methylaminobenzoic amide, indicated as formula (c);

ANT is O-aminobenzoic amide, indicated as formula (d);

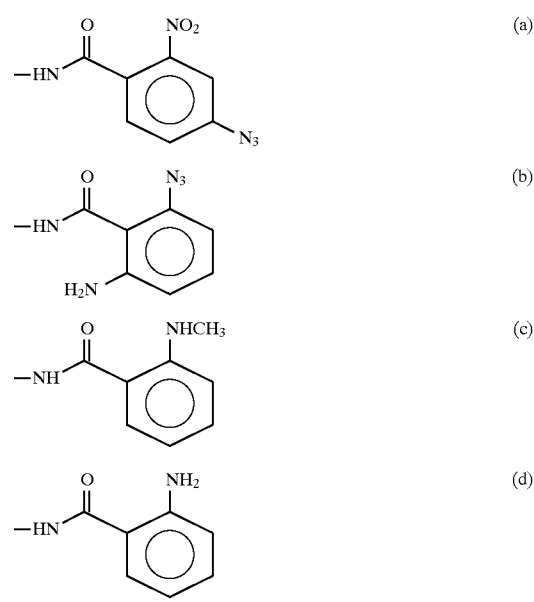

Among them, three kinds of compounds with the general formula II, III, IV are preferred.

The amino hydrogenated quinazoline compounds and derivatives thereof are compounds having following general formula II,

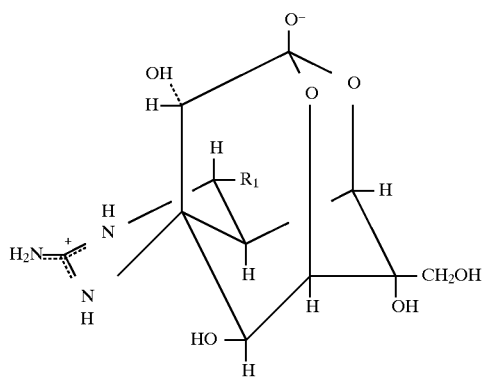

II

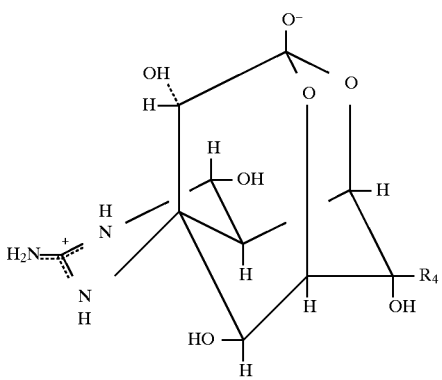

IV wherein:

$R_1$ can be selected from the group consisting of OH, an alkyl or a oxyalkyl with $C_1$–$C_4$, $NH_2$, NHR", NR"R"', among them R" and R"' can be an alkyl with $C_1$–$C_4$.

Among them, the more preferred compounds are:

Tetrodotoxin $R_1$=OH (1);

deoxytetrodotoxin $R_1$=H (2);

The amino hydrogenated quiniazoline compounds and derivatives thereof are compounds having following general formula III.

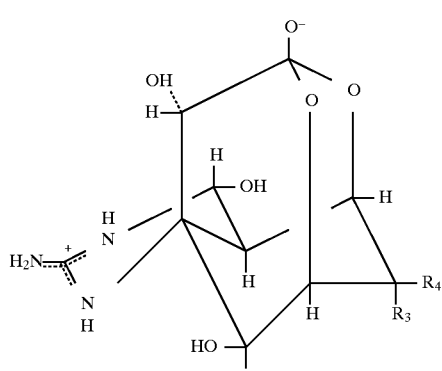

III wherein:

$R_3$, $R_4$ are =O, or when $R_3$ is H, $R_4$ is selected from the group consisting of:

$CH_2OH$,

CH(OH)NHOMe,

—NAP—gly,

—NAP—en,

—$CH_2NH_2$,

—$CH_2NHCH_3$,

—AAG,

—NMAG, and

—ANT.

Among them, the more preferred compounds are:

AAG-degradation Tetrodotoxin $R_4$=AAG (3);

NMAG-degradation Tetrodotoxin $R_4$=NMAG (4);

ANT-degradation Tetrodotoxin $R_4$=ANT (5); and, degradation Tetrodotoxin $R_3$, $R_4$ is =O (6).

The amino hydrogenated quinazoline and their derivatives are compounds having following general formula IV, wherein, $R_4$ can be selected from the group consisting of:

—CHO,

—$CH_2$—Gly,

—$CH_2$—β—Ala,

—$CH_2$—Lys,

—$CH_2$—en,

—$CH_2$—NAP—Lys

—$CH_2$—NAP—en,

—CH(OH)CH($NH_2$)COOH;

—NH($CH_2$)$_4$CH($NH_2$)COOH;

—$NHCH_2COOH$;

—$NHCH_2CH_2COOH$; and

—$NHCH_2CH_2NH_2$.

Among them, the more preferred compounds are:

oxytetrodotoxin $R_4$=CHO (7);

chiriquitoxin $R_4$=CH(OH)CH($NH_2$)COOH (8);

and the compounds with the substituted groups of $R_4$:

—NH($CH_2$)$_4$CH($NH_2$)COOH (9);

—$NHCH_2COOH$ (10);

—$NHCH_2CH_2COOH$ (11); and,

—$NHCH_2CH_2NH_2$ (12).

The above-mentioned amino hydrogenated quinazoline compounds and derivatives thereof, including Tetrodotoxin, could inhibit the morphine's-dependence withdrawal symptoms, and it is not addicted by the antagonists. It could effectively and promptly inhibit and allay the withdrawal symptoms and could dispel the restlessness of patients as use of these kinds of compounds with adequate dosage when the withdrawal response commences upto the most severe. The withdrawal symptoms of patients were allayed and disappeared from 5 to 30 min after accepted administration of the therapy. Patients could be quiet and almost feel numb in month, tongue and lips, however, no uneasy feeling. The numb counteracts the desire of patients for drugs, such as heroin. After several days maintenance (2–8 days, and generally 2–3 days ), it reaches the clinical de-addiction which shows as the withdrawal symptoms disappeared completely and the test of morphine in urine transforms to negative. After halt in using the above-mentioned amino hydrogenated quinazoline compounds and derivatives thereof, there is no dependence to them and no adverse and side effects. As using the above-mentioned amino hydrogenated quinazoline compounds and derivatives thereof to treat patients, no case developed sicchasia, vomiting, collapse or coma as with the use of other medicines. It also has no side effects as in the treatment of methadone and DHE.

The invention further involves any composition of medicines, which contains an effective dosage of above-mentioned amino hydrogenated quinazoline compounds and their derivatives, to leave off drug dependence. The amino hydrogenated quinazoline compounds and their derivatives in this invention could be made by now available technologies with pharmaceutically acceptable carriers, excipients and other additives to various forms, such as injections (including subcutaneous, intramuscular or intravenous) or oral form (including hypoglossal etc. However, because the orally effective dosage is much higher than (about 20 times) that of injections, injection is preferred. It is preferred to dissolve the above-mentioned amino hydrogenated quinazoline compounds and their derivatives in weak acid water solution, such as benzoic acid or acetic acid solution with pH being 4–5.

As using to clear off drug dependence, the effective dosage of above-mentioned amino hydrogenated quinazoline compounds and their derivatives is from 5 $\mu$g to 300 $\mu$g when injected by subcutaneous, intramuscular or intravenous.

The invention also involves any method to clear off drug dependence which uses effective dosage of above-mentioned aminoperhydroquinazoline compounds and their derivatives through oral or subcutaneous, intramuscular or intravenous injections.

Although the compounds of the invention used in clearing one off drug dependence are all severely toxic substances, the administered dosage of therapy is much lower than intravenously toxic dosage, such as the toxic dosage of TTX which is 300 $\mu$g/person.

It takes 3–5 days to clear one off the drug dependence of opium, heroin, morphine, cocaine, amphetamine (ice), dolandin, dihydroetorphine and methadone and this kind of addictable alkaloid when using the aminoperhydroquinazoline compounds and their derivatives of this invention alone or co-use them with other anti-addiction medicines. They do not induce addiction themselves but could clear one off drug dependence within a short time, with little toxic and side effects, and quick recovering of health (7–10 days).

BEST MODE FOR CARRYING OUT THE INVENTION

Example 1

3 mg compound (1), TTX, was dissolved in 200 ml injection used water which containing 9.4 g benzoic acid (pH=4) and distributed it to 100 parts. Each contains compound (1) 30 $\mu$g and be made as injections (1).

Example 2

15 mg compound (2), was dissolved in 200 ml pH 4 benzoic acid solution and distributed to 100 parts. Each contains compound (2) 150 $\mu$g and be made as injections (2).

Example 3–5

10 mg compound (3)–(5) was dissolved in 200 ml pH 4 acetic acid individually, then divided the solution into 100 parts to prepare injections (3)–(5), so each injection contained 100 $\mu$g compound (3)–(5).

Example 6

15 mg compound (6) was dissolved in 200 ml pH 4 benzoic acid, then divided the solution into 1100 parts to prepare injection (6), so each injection contained 150 $\mu$g compound (6).

Example 7

3 mg compound (7) was dissolved in 200 ml pH 5 benzoic acid, then divided the solution into 100 parts to prepare injection (7), so each injection contained 30 $\mu$g compound (7).

Example 8

3 mg compound (8) was dissolved in 200 ml pH 4 acetic acid, then divided the solution into 100 parts to prepare injection (8), so each injection contained 30 $\mu$g compound (8).

Example 9–12

6 mg compound (9)–(12) was dissolved in 200 ml pH 5 acetic acid individually, then divided the solution into 100 parts to prepare injections (9)–(12), so each injection contained 60 $\mu$g compound (9)–(12).

EXPERIMENT

Experiment 1: Comparison Experiment

Materials and Methods

1. Sample Collection 2768 cases with drug-dependence were collected in TTX de-addiction treatment, 2500 of them finished the whole process of treatment and 228 cases stopped the treatment because 206 cases could not tolerate the abstinence syndrome in the first 3 days and required to draw out this treatment, 17 cases were found in serious infectious diseases and other 5 cases were transferred to other hospitals.

These 2500 patients described above were 45–13 years old, averaged 23.5. Their drug-use period were 20–0.25 years, averaged 1.8 years. 2125 (85%) of them were male and 375 (15%) were female.

Kinds of drug-abuse: 831 cases taking Opium, 1570 cases taking Heroin, 41 cases taking Morphine, 50 cases taking DHE, 5 cases taking Dolantin, 2 cases taking Cocaine and 1 case taking Amphetamine.

Abuse routes: iv. 930, inhalation 1570.

Daily abuse amount were 5.0–0.1 g. Drug-addiction degree were preliminary divided as: Light (Group A), 1050 cases, 50 cases drawing out, 1000 cases finished the treatment of de-addiction; Medium (Group B), 1100 cases, 100 cases drawing out, 1000 cases finished the treatment of de-addiction; Serious(Group C), 568 cases,68 cases drawing out, 500 cases finished the treatment of de-addiction; Control(Group D), 60 cases randomly selected, 10 cases drawing out, 50 cases finished the treatment of de-addiction.

2. Accepted Cases Selection 2.1 Experiment Places and Case Resources

Experiment places were Health-Recovering Hospital and De-Drug-Addiction Agency recognized by China government. Accepted cases were de-addiction volunteers of drug-dependence on Opium, Morphine, Dolantin, Heroin, DHE, etc. Treatment formalities were voluntarily carried out by themselves or their families. Cases were free except drug-abuse during the treatment period.

2.2 Diagnostic Criterion

According to WHO drug-dependence definition and U.S.A DSM-III-R Criterion, the cases were diagnosed. Both their urine test and Naloxone addiction-press test were positive and their addiction syndrome were significant before TTX treatment.

3. De-Addiction Program Design 3.1 Grouping

The accepted cases were examined in detail, then according to their drug-taking period, amount, species, physical and mental conditions, they were divided into Light, Median and Serious 3 degrees and given general, intensive and special care.

4. Methods 4.1 Observation Methods 4.1.1 According to clinical abstinence syndrome and intensity and literature criterion, the cases were divided into III grades generally.

4.1.2 Given marks by abstinence syndrome frequency before and after treatment. Grade I 2×5; Grade II 3×6; Grade III 4×8.

4.1.3 Given marks by adverse reactions (see the table)before and after treatment.
  "1" known by requiring;
  "2" could be tolerated by chief complaint;
  "3" could not be tolerated, drug amount needed reducing;
  "4" stopped treatment.
4.1.4 Inhibition effect was marked as the sum of the above 2 items marks. The lower the mark, the better the inhibition effect; or the worse. Accepted cases were systematically examined, included system examination. Abstinence syndrome was marked on chief complaint and physical syndrome appearance. Laboratory examinations included test of blood, urine routine, liver function, electrocardiogram, X-ray for heart and lung, and drug urine test. Physical complication, psychosis and cardiovascular diseases patients were excluded after the treatment beginning. The treatment results were observed and recorded everyday and marked by a proper person. Everyday, after drug administration, cases were measured blood pressure, heart rate and marked on the adverse reactions. Each treatment period was set as 3–8 days. Treatment efficacy was evaluated as soon as the treatment finished, and the results were statistical analysis.
4.2 Treatment Methods
  Group A: TTX (from Case 1) treated;
  Group B: TTX+Diazepamum treated;
  Group C: TTX+Agonist treated;
  Group D: Control
  Among them:
  Group A: Cases of drug-taking less amount, shorter period, better physical conditions and stronger will, could be only treated by TTX i.m. 1 injection per day, for 3 days.
  Group B: Cases of drug-taking more amount, longer period, worse physical conditions and weaker will, could be treated by TTX with Diazepamum. In the first 3 days, i.m. or iv TTX 1–2 injections/day, bid., and iv. by drop Diazepamum 10–20 mg in 500 ml 5–10% glucose-normal saline after 4–6 hours of the first TTX administration, bid. Cases that still could not sleep were additionally administrated 50–100 mg Wintermin.
  Group C: Cases of drug-taking amount more than 2 g daily, period longer than 2 years and had abuse experience of Opium, DHE, Diazepamum, Wintermin etc. Their physical and mental conditions were worst. Their aim was generally to reduce but not to get rid of drug-abuse. For their treatment 2 methods were designed.
    Method C1: On day 1 to 5, i.m. TTX bid and on day 1 to 3, add agonist such as Methadone; day 1, 30–40 mg, day 2, 20–30 mg, day 3–4, 20 mg, day 5, 10 mg p.o.. On day 6–8, symptomatic treatment.
    Methods C2: On day 1–5, i.m. TTX bid, 2 hours later p.o. Diazepamum 10 mg, Clozapinum 25 mg. More serious cases were iv. by drop 50–100 mg Wintermin in 5–10% glucose-normal saline after the first TTX 2 injections. It was also suggested that p.o. estazolam 3–4 mg /day, or p.o. Clonozepam 6–10 mg/day to sustain 3–4 days then the dosage gradually reduced till day 7.
  Group D: divided to 2 methods:
    D1: Methadone p.o.;
    D2: DHE iv. or p.o..
    Daily dosage of each group see Tab. 1.
  Results
1. Criterion
  In this program, all observations of therapeutic efficacy were recorded in time everyday and quantified in a table to give marks, which was also referred to chief complaints to certain the criterion of treatment effect.

1.1 Significantly effective: Physical syndrome disappeared, mental syndrome alleviated obviously. Marks were lower than 25 in 72 hours and lower than 10 at the end of the treatment.
1.2 Effective: Physical syndrome and mental syndrome reduced. Marks were lower than 60 in 72 hours and lower than 25 at the end of the treatment.
1.3 Not effective: Cases had no or just slight reduction of physical syndrome. Their mental syndrome was still obvious. Marks were more than 60 in 72 hours and more than 25 at the end of the treatment, or stopping drug administration during the treatment.
2. Evaluation of Efficacy
2.1 After drug administration the treatment groups showed significant inhibition effect on the generation and reaction intensity of abstinence syndrome. The therapeutic effects were highly significantly different from control group in 72 hours and at the end of the treatment ($p<0.01$). (see Tab.2.)
2.2 Inhibition Effect on Various Intensity of Abstinence Syndrome
  See Tab.3. The total syndrome marks of 6 groups were not statistically different ($p>0.05$) before the treatment, while there were significant difference in mark reduction in 72 hours treatment ($p<0.01$), but there were no difference in total mark reduction in group A,B and C1,C2 after 72 hours treatment ($p>0.05$).
2.3 Inhibition Effect on Various Abstinence Syndrome
  Comparing the frequency of various abstinence syndrome before and after the treatment, treatment groups showed significant reduction in 15 min. and after 72 hours treatment, especially in Group A,B. Treatment results of various abstinence syndrome see Tab. 4.
3. Comparison of Time of Onset of Drug Effect.
  All accepted cases were administrated drugs when various abstinence syndrome reached its peak (syndrome mark more than 20). Noticed the time point of abstinence syndrome significant alleviated or disappeared. The results are as fellows:

| | | | |
|---|---|---|---|
| TTX i.m. | 3–20 min. | Mean: | 8.00 ± 2.00 min. |
| TTX iv. by drop | 2–15 min. | Mean: | 5.40 ± 1.20 min. |
| DHE i.m. | 7–25 min. | Mean: | 10.54 ± 4.50 min. |
| DHE i.v. by drop | 5–20 min | Mean: | 13.11 ± 4.12 min |
| Methadone p.o. | 50–90 min. | Mean: | 71.00 ± 21.86 min. |

TTX showed its effect was faster than control drug whatever the administration routes.
4. Gradual Changes of Hamilton Anxiety
  Results see Tab. 5.
  The change tendency of Hamilton anxiety was closely related to its abstinence syndrome in each group. Mark of 6 groups was all reduced after treatment, group A,B,C 1 ,C2 was plateaued; on day 4,5, Group D2 elevated then reduced gradually; while Group D1 was elevated on day 8–10 after administration stopping. All of Group A,B and C showed significantly different from Group D ($p<0.05$ or $p<0.01$).
5. Drug Adverse Reactions
  No adverse reactions were found in Group A,B,C 1,C2,D1 and D2. No abnormality was found in blood, liver, kidney function and electrocardiogram before and after treatment. Urine drug amount and Naloxone addiction-press test were all negative after the treatment.
  Most cases in Group A treated with TTX had the feeling of numbness in tong tip and lips. So did small number of group B and only a few of group C.
  Some cases in Group D2, D1 treated with DHE and Methadone had the syndrome of dizzle, cardiopalmus, nausea and hidrosis etc.

Almost every serious cases felt systematic pain, tiredness at the later phase of the de-abstinence treatment.

6. De-experiment Rate

Some cases drew out the experiment during the treatment process. The rate in Group A was about 5%, Group B 10%, Group C1 12%, Group C2 15%, Group D1 15%, Group D2 35%.

Experiment 2: Typical Cases

Cases 1–20

Tab. 6 showed of the sex, drug-dependent species, drug-taking period and routes of typical case 1–20, and the treatment dosage and days of administration of the injections (Example 1–8) according to the present invention. Tab. 7 showed cases abstinence syndrome before treatment, including subjective and objective syndrome. Tab. 8 showed de-addiction situations after the compounds administration 5–15 min. and 4 days. It suggested that the compounds according to the present invention could get rid of addiction rapidly with less side effects.

Industrial Applicability

In this invention the discovery of new uses for the titled compounds suggests that this type of compounds can be used to prepare drugs for treatment of human drug-dependence.

TABLE 1

Daily Dosage of TTX and Control Group

| Administration Days | Group A TTX, im, $\mu$g n = 1000 | Group B TTX, im, $\mu$g n = 1000 | Group C | | Group D | |
|---|---|---|---|---|---|---|
| | | | C1 TTX, im/iv, $\mu$g | C2 TTX, im/iv, $\mu$g | D1 Methadong, po, mg | D2 DHE, $\mu$g |
| d1 | 30 | 60 | 60 + Methadone 30 mg po | 60 + Diazepamum 10 mg + Clorozapimum 25 mg | 30 | 400 iv |
| d2 | 30 | 60 + Diazepamum 10–20 mg in 500 ml Glucose + N.S | 60 + Methadone 30 mg po | 60 + Diazepamum 10 mg + Clorozapimum 25 mg | 30 | 400 iv |
| d3 | 30 | 60 + Diazepamum 10–20 mg in 500 ml Glucose + N.S | 60 + Methadone 30 mg po | 60 + Diazepamum 10 20 mg po Clorozapimum 25 mg | 30 | 400 iv |
| d4 | | 60 | 60 + Methadone 30 mg po | 60 + Diazepamum 10 mg + Clorozapimum 25 mg | 20 | 350 po |
| d5 | | 30 | 30 + Methadone 10 mg po | 60 + Diazepamum 10 mg + Clorozapimum 25 mg | 15 | 300 po |
| d6 | | 30 | 30 + Methadone 10 mg po | 30 + Diazepamum 10 mg | 15 | 200 po |
| d7 | | | 30 | 30 + Diazepamum 10 mg | 10 | 150 po |
| d8 | | | | | 5 | 100 po |

TABLE 2

Comparison of Curative Effect between Treatment Groups and Control Group

| | | Efficacy in 72 h | | | Final Efficacy | | Effective |
|---|---|---|---|---|---|---|---|
| Group | Case Number | Significant effective | Effective | Not effective | Significant effective | Effective | Not effective | Rate (%) |
| A | 1000 | 970 | 30 | 0 | 950 | 50 | 0 | 100 |
| B | 1000 | 750 | 240 | 10 | 510 | 488 | 2 | 98.8 |
| C1 | 250 | 100 | 125 | 25 | 75 | 170 | 5 | 98 |
| C2 | 250 | 80 | 120 | 50 | 60 | 183 | 7 | 97.2 |
| D1 | 20 | 10 | 8 | 2 | 5 | 14 | 1 | 95 |
| D2 | 20 | 12 | 6 | 2 | 6 | 13 | 1 | 95 |

TABLE 3

Changes of Evaluating Maks on Withdrawal Syndrome

|  |  |  | Group C | | Group D | |
|---|---|---|---|---|---|---|
| Date | Group A | Group B | C1 | C2 | D1 | D2 |
| before treatment | 10.0 ± 0 | 16.5 ± 2.3 | 25.4 ± 3.2 | 25.5 ± 3.3 | 17.4 ± 7.9 | 17.4 ± 2.0 |
| d1 | 5.0 ± 1.5 | 11.6 ± 1.4 | 16.8 ± 4.2 | 12.7 ± 2.9 | 11.0 ± 3.0 | 5.1 ± 3.2 |
| d2 | 3.5 ± 1.5 | 8.3 ± 1.9 | 9.6 ± 2.5 | 9.9 ± 2.5 | 10.0 ± 2.9 | 4.5 ± 3.3 |
| d3 | 1.9 ± 1.3 | 6.0 ± 2.0 | 9.5 ± 2.3 | 8.0 ± 2.7 | 8.1 ± 2.6 | 3.3 ± 2.5 |
| d4 |  | 4.4 ± 1.8 | 7.1 ± 1.3 | 6.2 ± 2.1 | 7.3 ± 2.3 | 6.5 ± 3.7 |
| d5 |  | 1.6 ± 1.5 | 5.1 ± 1.7 | 5.2 ± 1.8 | 5.5 ± 2.1 | 5.5 ± 2.9 |
| d6 |  |  | 4.3 ± 1.4 | 4.3 ± 1.7 | 4.4 ± 1.5 | 4.3 ± 1.2 |
| d7 |  |  | 1.6 ± 1.4 | 1.6 ± 1.5 | 2.1 ± 1.6 | 3.1 ± 1.5 |
| d8 |  |  | 1.3 ± 1.5 | 1.3 ± 1.4 | 4.5 ± 1.0 | 2.8 ± 1.7 |

TABLE 4

Evaluating Marks on Withdrawal Syndrom before and after Treatment

| Withdrawal syndrome | Group A before (15 min) after 72 hrs | Group B before (15 min) after 72 hrs | Group C1 before (15 min) after 72 hrs | Group C2 before (15 min) after 72 hrs | Group D1 before (15 min) after 72 hrs | Group D2 before (15 min) after 72 hrs |
|---|---|---|---|---|---|---|
| Lacrimation | 983(81)1 | 985(180)120 | 246(210)171 | 245(208)71 | 19(20)17 | 18(3)19 |
| Salivation | 980(40)31 | 1000(112)101 | 250(167)198 | 250(200)77 | 20(20)18 | 19(3)20 |
| Yawns | 921(450)21 | 999(720)57 | 250(172)98 | 250(198)42 | 20(20)16 | 20(10)20 |
| Insomnia | 998(350)98 | 998(620)512 | 250(160)198 | 25(220)72 | 19(19)17 | 19(18)18 |
| Gooseflesh | 921(80)2 | 958(120)81 | 245(42)25 | 246(41)41 | 17(19)18 | 18(18)18 |
| Vomiting | 142(0)0 | 167(34)11 | 47(40)3 | 50(41)0 | 7(8)8 | 4(1)8 |
| Nausea | 640(0)0 | 941(100)20 | 236(41)7 | 225(40)3 | I5(17)15 | 14(7)11 |
| Anorexia | 945(400)41 | 958(801)122 | 241(202)51 | 240(240)230 | 18(19)20 | 19(17)19 |
| Anxiet and restlessness | 998(151)123 | 998(670)210 | 250(240)50 | 250(210)17 | 19(20)19 | 18(17)20 |
| Systemic Pain | 888(101)140 | 966(121)720 | 248(240)247 | 241(240)247 | 17(19)18 | 17(13)18 |
| Abdominal-gia & diarrhea | 850(32)21 | 900(401)126 | 247(128)33 | 235(131)17 | I5(16)14 | 16(16)17 |
| Muscular tremors | 683(121)90 | 590(252)257 | 130(60)57 | 150(48)12 | 11(11)13 | 10(13)17 |
| Rapid pulse | 830(71)3 | 835(307)123 | 213(200)35 | 215(147)35 | 10(14)18 | 10(14)19 |
| Cold & hot | 958(21)0 | 960(25)3 | 249(120)7 | 245(98)8 | 18(20)19 | 17(14)18 |
| Pupil (mm) | 2.8 ± 0.3 1.4 ± 0.8 | 2.9 ± 0.8 1.8 ± 0.5 | 2.3 ± 0.5 1.3 ± 0.7 | 2.8 ± 0.5 1.9 ± 1.0 | 2.5 ± 0.4 1.9 ± 1.1 | 2.4 ± 0.7 1.7 ± 0.7 |
| Weakness | 767(667)672 | 880(701)8.08 | 245(245)246 | 225(224)248 | 15(17)19 | 18(7)19 |
| Thirsting for | 999(450)720 | 1000(661)881 | 250(249)125 | 250(230)247 | 20(20)20 | 20(19)20 |

DSM-III-R Diagnostic Criterion

TABLE 5

Changes of the Evaluating Marks (HAMA) on Anxiety Symptom

| Date | Group A n = 1000 X ± S | Group B n = 1000 X ± S | Group C1 n = 250 X ± S | Group C2 n = 250 X ± S | Group D1 n = 20 X ± S | Group D2 n = 20 X ± S |
|---|---|---|---|---|---|---|
| before treatment | 22 ± 4 | 24 ± 5 | 25 ± 5 | 22 ± 4 | 22 ± 4 | 22 ± 4 |
| after treatment d1 | 11 ± 5 | 13 ± 6 | 11 ± 5 | 18 ± 5 | 11 ± 5 | 3.3 ± 2.5 |
| d2 | 8 ± 4 | 11 ± 5 | 8 ± 5 | 11 ± 5 | 8 ± 5 | 3.2 ± 2.5 |
| d3 | 7 ± 3 | 10 ± 4 | 5.1 ± 2.8 | 10 ± 4 | 5 ± 3 | 2.3 ± 1.5 |
| d4 | 4 ± 3 | 8 ± 4 | 4.8 ± 2.8 | 7 ± 3 | 4.8 ± 3 | 8 ± 5 |
| d5 | 3 ± 2 | 4 ± 2 | 4 ± 3 | 5 ± 7 | 4 ± 3 | 6 ± 3 |
| d6 |  | 3 ± 2 | 4 ± 3 | 4 ± 3 | 0 ± 3 | 0.7 ± 2.7 |
| d7 |  |  | 6.4 ± 2.2 | 3.5 ± 2.5 | 5.3 ± 2 | 4.9 ± 2.6 |
| d8 |  |  | 7.0 ± 2.7 | 3 ± 2.5 | 4 ± 2.5 | 4.5 ± 3.0 |

TABLE 6

Dosage of the Compound According to the Present Invention for De-addiction
(Treatment Results of 20 Typical Cases)

| Case No. | Sex | Drug type | Using Period (year) | Drug Dosage (g/day) | Drug route of use | De-addiction Comp. | Dosage | Route of use | Administration days |
|---|---|---|---|---|---|---|---|---|---|
| 1 | male | Herion | 4 | 0.2 | iv | (1) | 30 μg × 10 | im | 5 |
| 2 | male | Opium | 4 | 0.4 | inhalate | (2) | 150 μg × 8 | im | 3 |
| 3 | male | Opium | 1 | 0.4 | inhalate | (3) | 100 μg × 5 | im | 2 |
| 4 | male | Herion | 7 months | 1.0 | inhalate | (4) | 100 μg × 4 | im | 3 |
| 5 | male | Herion | 3 | 1.0 | inhalate | (5) | 100 μg × 8 | im | 4 |
| 6 | male | Herion | 1 | 1.0 | inhalate | (6) | 150 μg × 5 | im | 3 |
| 7 | female | Herion | 1.6 | 0.8 | iv | (7) | 30 μg × 8 | iv | 6 |
| 8 | male | Opium | 1 | 0.2 | inhalate | (8) | 30 μg × 7 | im | 3 |
| 9 | male | Opium | 4 | 0.8 | inhalate | (9) | 60 μg × 6 | im | 4 |
| 10 | male | Herion | 4 | 1.0 | inhalate | (10) | 60 μg × 6 | im | 3 |
| 11 | male | Herion | 5 | 0.4 | inhalate | (11) | 60 μg × 10 | im | 3 |
| 12 | male | Herion | 4 | 1.0 | inhalate | (12) | 60 μg × 12 | im | 6 |
| 13 | male | Herion | 5 | 1.2 | iv | (8) | 30 μg × 11 | iv | 4 |
| 14 | male | Herion | 9 | 0.5 | inhalate | (11) | 60 μg × 4 | im | 4 |
| 15 | male | Herion | 5 | 1.5 | iv | (12) | 60 μg × 13 | iv | 4 |
| 16 | male | Herion | 1 | 0.5 | iv | (10) | 60 μg × 5 | im | 3 |
| 17 | male | Opium | 5 | 1.5 | inhalate | (2) | 150 μg × 5 | im | 5 |
| 18 | male | Opium | 20 | 1.2 | inhalate | (3) | 100 μg × 3 | im | 5 |
| 19 | male | Herion | 2 | 2.5 | inhalate | (1) | 30 μg × 7 | im | 7 |
| 20 | male | Herion | 5 | 3.5 | iv | (1) | 30 μg × 8 | iv | 6 |

TABLE 7

Withdrawal Syndrome of the Patients before Using the Compound of the Present Invention

| Case No. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Subjective symptom | | | | | | | | | | | | | | | | | | | | |
| Agitating | + | + | + | + | + | + | + |   | + | + | + | + | + |   | + | + | + | + | + | + |
| Joint pain |   | + | + | + |   | + |   | + | + | + | + |   | + | + |   |   |   |   |   |   |
| Cold | + | + | + | + | + | + | + | + | + | + | + | + |   | + | + | + | + | + | + | + |
| Insomnia | + | + | + | + | + | + | + | + | + | + | + | + | + | + | + | + | + | + | + | + |
| Exciting | + |   | + |   |   |   |   | + |   |   |   | + |   |   |   |   |   |   |   |   |
| Thirsty | + | + | + |   | + |   |   |   |   | + |   | + |   | + |   | + |   | + |   |   |
| Dyspnea | | | | | | | | | | | | | | | | | | | | |
| Headache |   | + |   |   | + |   |   |   | + | + |   |   |   | + |   |   |   | + | + |   |
| Abdominal pain | + |   | + |   | + | + | + | + |   |   | + | + |   | + |   |   | + | + |   | + |
| Nausea |   | + | + | + |   | + | + | + |   |   | + | + |   | + |   |   | + | + |   | + |
| Lower extremity sore | + |   |   | + | + |   | + | + |   | + |   | + | + |   | + | + | + |   |   |   |
| Thoracic depress |   | + |   | + |   | + |   | + |   |   |   | + | + |   |   |   |   |   | + |   |
| Stomachache | + |   | + |   | + | + |   |   |   |   |   |   |   |   |   |   |   |   | + |   |

TABLE 7-continued

Withdrawal Syndrome of the Patients before Using the Compound of the Present Invention

| Case No. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Objective symptom | | | | | | | | | | | | | | | | | | | | |
| Yamns | + | + | + | + | + | + | + | + | + | + | + | + | + | + | + | + | + | + | + | + |
| Skin itch | + | + | | + | | | | + | | | + | + | | | + | + | | | + | + |
| Lacrimation | + | + | + | + | + | + | + | + | + | + | + | + | + | + | + | + | + | + | + | + |
| Finger-tremors | | + | | | + | + | | + | + | + | | | | + | | + | | | | |
| Rhinorrhea | + | + | + | + | + | + | + | + | + | + | + | + | + | + | + | + | + | + | + | + |
| Mydriasis | + | | + | | | | | | + | | | | | | + | | | | | + |
| Miosis | | + | | | | | | | | | | | | | | | | | | |
| Vomiting | | + | + | + | | + | | + | | | | | | | + | + | + | | + | + |
| Dysentery | + | | | | + | | + | | | + | | | | | | | | | | |
| Nausea | | + | | + | | + | + | | | + | + | | | + | | | | + | | + |
| Salivation | + | + | + | + | + | + | + | + | + | + | + | + | + | + | + | + | + | + | + | + |
| Toss about | + | + | | | | + | | | | | | | | + | | + | | | + | |
| Feet agitating | | | | + | + | | | | | | | | | | | | | | | |
| Borborygmi | + | + | | | | | | | + | | | | | + | | + | | + | | |
| Cough | | + | + | + | + | + | | | | | | | | | | + | | | | |
| Disturbance | | | + | | | | + | | + | | | | | + | | | | | | |
| Groan | + | + | | | | + | | | + | | | | | + | | | | | | |
| Diaphoresis | + | | | | | | | | | | | | | | | | | | | |
| Proteinuria | + | + | | + | + | + | | | | + | + | | | | + | | | + | + | + |
| Respiring number/min | 20 | 20 | 18 | 20 | 20 | 20 | 20 | 20 | 20 | 20 | 18 | 20 | 20 | 20 | 20 | 20 | 20 | 20 | 20 | 20 |
| Pulse | 88 | 84 | 80 | 88 | 82 | 90 | 90 | 84 | 88 | 84 | 80 | 72 | 84 | 82 | 76 | 90 | 90 | 84 | 84 | 88 |
| Blood pressure | 90/60 | 100/70 | 100/70 | 90/80 | 90/60 | 90/60 | 90/60 | 100/70 | 96/70 | 90/60 | 100/70 | 100/80 | 100/70 | 90/60 | 96/68 | 100/70 | 90/60 | 90/60 | 90/80 | 90/70 |

TABLE 8

Efficacy of De-addiction of the Patients after Using the Compounds of the Preseng Invention After injecting the Compound (5–15 min)

| Case | Pure numbness in tongue, month and lips | Pure numbness in arms and legs | Subjective sense | Pulse rate (no significant changes in blood pressure after injection) | d4 Morphine in urine |
|---|---|---|---|---|---|
| 1 | (+) | | fine | 74 | (-) |
| 2 | (+) | (+) | fine | 78 | (-) |
| 3 | (+) | (+) | fine | 78 | (-) |
| 4 | (+) | | not fine | 86 | (-) |
| 5 | (+) | (+) | fine | 80 | (-) |
| 6 | (+) | | fine | 86 | (-) |
| 7 | (+) | | fine | 86 | (-) |
| 8 | (+) | | fine | 80 | (-) |
| 9 | (+) | | fine | 82 | (-) |
| 10 | (+) | (+) | fine | 80 | (-) |
| 11 | (+) | | fine | 76 | (-) |
| 12 | (+) | | fine | 70 | (+) |
| 13 | (+) | (+) | fine | 80 | (-) |
| 14 | (+) | | fine | 78 | (-) |
| 15 | (+) | | fine | 74 | (+) |
| 16 | (+) | (+) | fine | 86 | (+) |
| 17 | (+) | | fine | 84 | (-) |
| 18 | (+) | | fine | 80 | (-) |
| 19 | (±) | (±) | fine | 84 | (-) |
| 20 | (+) | | fine | 84 | (+) |

We claim:

1. A method of treating drug dependence in a human which comprises administering to the human suffering from drug dependence at least one amino hydrogenated quinazoline having the general formula I in an amount effective to cause said drug dependent human to abstain from drug-dependence

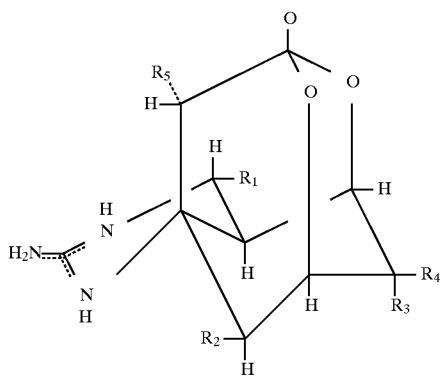

wherein $R_2$ and $R_5$ each is selected from the group consisting of H, OH, and OAc; $R_1$ is selected from the group consisting of H, $C_1$–$C_4$ alkyl, OH, OR, OC(O)R', $NH_2NHR''$, and NR''R''' wherein R is $C_1$–$C_6$ alkyl, R' is $C_1$–$C_3$ alkyl, and R'', and R''' is $C_1$–$C_4$ alkyl;

$R_3$ and $R_4$ are =O; or when $R_3$ is H, $R_4$ is selected from the group consisting of:
—ROH, wherein R is a branched or straight chain $C_1$–$C_7$ alkyl,
—CH(OH)NHOMe,
—NAP—gly,
—NAP—en,
—$CH_2NH_2$,
—$CH_2NHCH_3$,
—AAG,
—NMAG, and
—ANT;

or when $R_3$ is OH or OC(O)R wherein R is $C_1$–$C_3$ alkyl, $R_4$ is selected from the group consisting of
—CHO,
—$CH_2$—gly,
—$CH_2$—β—Ala,
—$CH_2$—Lys,
—$CH_2$—en,
—$CH_2$—NAP—Lys,
—$CH_2$—NAP—en,
—CH(OH)CH($NH_2$)COOH,
—NH($CH_2$)$_n$COOH,
—NH($CH_2$)$_n$$NH_2$ and
NH($CH_2$)$_n$CH($NH_2$)COOH wherein:
n=1–6,
en is ethylene,
NAP is 4-triazo-2-nitrobenzoic amide,
AAG is 2-triazo-O-aminobenzoic amide,
NMAG is O-methylaminobenzoic amide,
ANT is O-aminobenzoic amide.

2. The method according to claim 1, wherein the amino hydrogenated quinazoline compounds and derivatives thereof are compounds having the following general formula II,

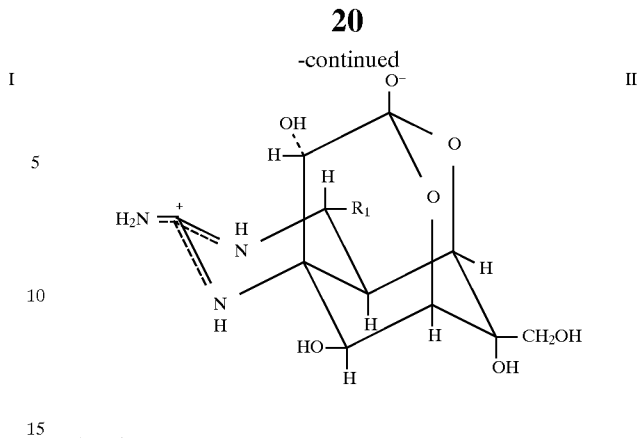

wherein $R_1$ can be selected from the group consisting of OH, H, an alkyl or a oxyalkyl with $C_1$–$C_4$, $NH_2$, NHR'', NR''R''', among them R'' and R''' can be an alkyl with $C_1$–$C_4$.

3. The method according to claim 1, wherein the amino hydrogenated quinazoline compounds and derivatives thereof are compounds having the following general formula III,

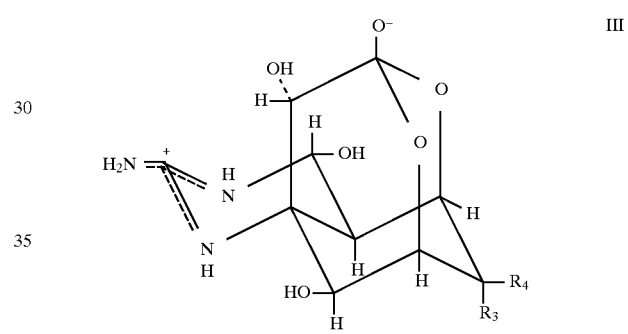

wherein:

$R_3$, $R_4$ are =O, or when $R_3$ is H, $R_4$ is selected from the group consisting of:
—$CH_2OH$,
—CH(OH)NHOMe,
—NAP—gly,
—NAP—en,
—$CH_2NH_2$,
—$CH_2NHCH_3$,
—AAG,
—NMAG, and
—ANT;

wherein, en, NAP, AAG, NMAG and ANT have the same definitions as stated above.

4. The method according to claim 1, wherein the amino hydrogenated quinazoline and their derivatives are compounds having the following general formula IV,

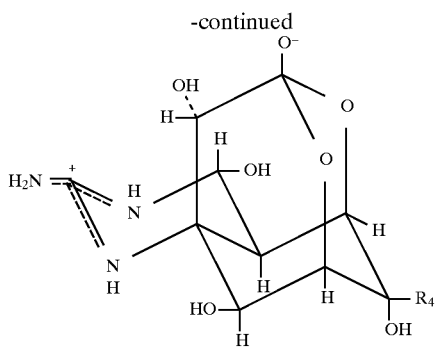

wherein, $R_4$ can be selected from the group consisting of:
—CHO,
—$CH_2$—Gly,
—$CH_2$—β—Ala,
—$CH_2$—Lys,
—$CH_2$—en,
—$CH_2$—NAP—Lys
—$CH_2$—NAP—en,
—CH(OH)CH($NH_2$)COOH;
—NH($CH_2$)$_4$CH($NH_2$)COOH;
—NH$CH_2$COOH;
—NH$CH_2$$CH_2$COOH; and
—NH$CH_2$$CH_2$$NH_2$,
wherein en and NAP have the same definition as stated above.

5. The method according to claim 2, wherein the group $R_1$ of the amino hydrogenated quinazoline compounds and derivatives thereof is —OH.

6. The method according to claim 2, wherein the group $R_1$ of the amino hydrogenated quinazoline compounds and derivatives thereof is H.

7. The method according to claim 3, wherein the group $R_3$ of the amino hydrogenated quinazoline compounds and derivatives thereof is AAG.

8. The method according to claim 3, wherein the group $R_4$ of the amino hydrogenated quinazoline compounds and derivatives thereof is NMAG.

9. The method according to claim 3, wherein the group $R_4$ of the amino hydrogenated quinazoline compounds and derivatives thereof is ANT.

10. The method according to claim 3, wherein the group $R_3$, $R_4$ of the amino hydrogenated quinazoline compounds and derivatives thereof is =O.

11. The method according to claim 4, wherein the group $R_4$ of the amino hydrogenated quinazoline compounds and derivatives thereof is —CHO.

12. The method according to claim 2, wherein the group $R_4$ of the amino hydrogenated quinazoline compounds and derivatives thereof is CH(OH)CH($NH_2$)COOH.

13. The method according to claim 4, wherein the group $R_4$ of the amino hydrogenated quinazoline compounds and derivatives thereof is NH($CH_2$)$_4$—CH($NH_2$)COOH.

14. The method according to claim 4, wherein the group $R_4$ of the amino hydrogenated quinazoline compounds and derivatives thereof is NH$CH_2$COOH.

15. The method according to claim 4, wherein the group $R_4$ of the amino hydrogenated quinazoline compounds and derivatives thereof is NH$CH_2$$CH_2$COOH.

16. The method according to claim 4, wherein the group $R_4$ of the amino hydrogenated quinazoline compounds and derivatives thereof is NH$CH_2$$CH_2$$NH_2$.

17. A method for treating a human suffering from drug dependence, comprising administering to said human a daily dosage between 5 and 300 μg of at least one compound of formula I:

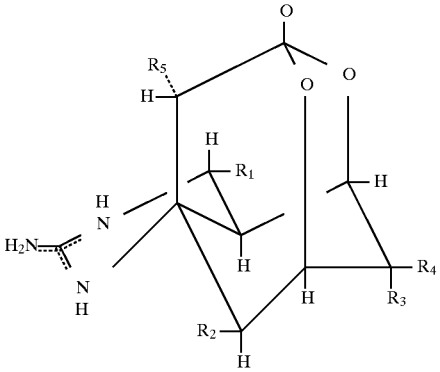

wherein
$R_2$ and $R_5$ each is selected from the group consisting of H, OH, and OAc; $R_1$ is selected from the group consisting of H, $C_1$–$C_4$ alkyl, OH, OR, OC(O)R', $NH_2$NHR", and NR"R"' wherein R is $C_1$–$C_6$ alkyl, R' is $C_1$–$C_3$ alkyl, and R" and R"' are $C_1$–$C_4$ alkyl;
$R_3$ and $R_4$ are =O or when $R_3$ is H, $R_4$ is selected from the group consisting of:
—ROH, wherein R is a branched or straight chain $C_1$–$C_7$ alkyl,
—CH(OH)NHOMe,
—NAP—gly,
—NAP—en,
—$CH_2$$NH_2$,
—$CH_2$NH$CH_3$,
—AAG,
—NMAG, and
—ANT;
or wherein $R_3$ is OH or OC(O)R wherein R is a $C_1$–$C_3$ alkyl and $R_4$ is selected from the group consisting of
—CHO,
—$CH_2$—gly,
—$CH_2$—β—Ala,
—$CH_2$—Lys,
—$CH_2$—en,
—$CH_2$—NAP—Lys,
—$CH_2$—NAP—en,
—CH(OH)CH($NH_2$)COOH,
—NH($CH_2$)$_n$COOH,
—NH($CH_2$)$_n$$NH_2$ and
—NH($CH_2$)$_n$CH($NH_2$)COOH;
wherein
n=1–6,
en is ethylene,
NAP is 4-triazo-2-nitrobenzoic amide,
AAG is 2-triazo-O-aminobenzoic amide,
NMAG is O-methylaminobenzoic amide,
ANT is O-aminobenzoic amide.

18. The method according to claim 17 wherein the method of administration is selected from the group consisting of oral, subcutaneous, intramuscular and intravenous administration.

19. The method according to claim 1, wherein said amino hydrogenated quinazoline is tetrodotoxin.

20. The method according to claim 17, wherein said amino hydrogenated quinazoline is tetrodotoxin.

21. The method according to claim 1, wherein said drug dependence is opioid drug dependence.

22. The method according to claim 17, wherein said drug dependence is opioid drug dependence.

* * * * *